US006248891B1

(12) United States Patent
Sharp et al.

(10) Patent No.: US 6,248,891 B1
(45) Date of Patent: Jun. 19, 2001

(54) SYNTHESIS OF ACRIDINE DERIVATIVE MULTIDRUG-RESISTANT INHIBITORS

(75) Inventors: Matthew Jude Sharp, Apex; Catherine J. Mader, Durham, both of NC (US); Calum Strachan, Montrose (GB)

(73) Assignee: Glaxo Wellcome, Inc., Research Triangle Park, NC (US)

( * ) Notice: Subject to any disclaimer, the term of this patent is extended or adjusted under 35 U.S.C. 154(b) by 0 days.

(21) Appl. No.: 09/403,158

(22) PCT Filed: May 22, 1998

(86) PCT No.: PCT/EP98/02991

§ 371 Date: Jan. 19, 2000

§ 102(e) Date: Jan. 19, 2000

(87) PCT Pub. No.: WO98/52923

PCT Pub. Date: Nov. 26, 1998

(30) Foreign Application Priority Data

May 23, 1997 (GB) .................................................. 9710612

(51) Int. Cl.[7] .................................................. C07D 219/06
(52) U.S. Cl. .............................................................. 546/103
(58) Field of Search ................................................ 546/103

(56) References Cited

U.S. PATENT DOCUMENTS 5,604,237 * 2/1997 Dumaitre et al. ..................... 514/297

FOREIGN PATENT DOCUMENTS

494623 * 7/1992 (EP) .
9212132 * 7/1992 (WO) .
9611007 * 4/1996 (WO) .

OTHER PUBLICATIONS

Williams et al. *Biologically Active Peptides: Design, Synthesis, and Utilization*, vol. 1, p. 140–141 (1993).*
Nerina Dodic et al., Synthesis and Activity Against Multidrug Resistance in Chinese Hamster Ovary Cells of New Acridone–4–Carboxamides, J. Med. Chem. 38, 2418–2426, 1995.*
Louis A. Coupino. 1–Hydroxy–7–azabenzotriazde. An Efficient Peptide Coupling Additive. J. Am. Chem. Soc. 115 4397, 1993.*

* cited by examiner

Primary Examiner—Deborah C. Lambkin
Assistant Examiner—Sonya Wright
(74) Attorney, Agent, or Firm—John L. Lemanowicz

(57) ABSTRACT

Synthesis of the MDRI of formula (I) from intermediates of acridone acid of formula (II) and aminophenethyl isoquinoline of formula (III), via steps including coupling and conversion to yield the MDRI of formula (I).

8 Claims, No Drawings

SYNTHESIS OF ACRIDINE DERIVATIVE MULTIDRUG-RESISTANT INHIBITORS

This application is filed pursuant to 35 U.S.C. § 371 as a United States National Phase Application of International Application No. PCT/EP98/02991 filed May 22, 1998, which claims priority from GB 9710612.4 filed May 23, 1997.

BACKGROUND OF THE INVENTION

This invention relates to an improved process for preparing acridine derivatives. In particular it relates to the synthesis of compounds which are capable of sensitizing multidrug-resistant cancer cells to chemotherapeutic agents.

The multidrug-resistant inhibitor (MDRI), chemically known as N-{4-[2-(1,2,3,4-tetrahydro-6,7-dimethoxy-2-isoquinolinyl)-ethyl]phenyl}-9,10-dihydro-5-methoxy-9-oxo-4-acridine carboxamide and its physiologically acceptable salts is described in World Patent Application WO 92/12132, filed in the name of Laboratories Glaxo S.A. and published Jul. 23, 1992 and also described in World Patent Application WO 96/11007, filed in the name of Glaxo Wellcome Inc. and published Apr. 18, 1996. The compounds are disclosed as being useful in sensitizing multidrug-resistant cancer cells to chemotherapeutic agents.

In WO 92/12132, an acridine derivative was disclosed as synthesized by reacting compounds in the presence of coupling reagents commonly used in peptide synthesizing. The coupling reagents disclosed included dicyclohexylcarbodiimide (optionally in the presence of 1-hydroxybenzotriazole), diphenylphosphoryl azide or N,N-carbonyidiimidazole. Suitable inert solvents for the reaction included an ether, halogenated hydrocarbons, amides or ketones.

The synthesis of N-{4-[2-(1,2,3,4-tetrahydro-6,7-dimethoxy-2-isoquinolinyl)-ethyl]phenyl}-9,10-dihydro-5-methoxy-9-oxo4-acridine carboxamide and its physiologically acceptable salts and solvates is also disclosed by Ne'rina Dodic et al., Journal of Medicinal Chemistry, 1995, Vol. 38 No. 13, pages 2418–2426. The synthesis route in Dodic utilized the same coupling reagents as set forth in WO 92/12132. In the Dodic article, example 84 corresponds to N-{4-[2-(1,2,3,4-tetrahydro-6,7-dimethoxy-2-isoquinolinyl)ethyl]phenyl}-9,10-dihydro-5-methoxy-9-oxo-4-acridine carboxamide.

SUMMARY OF THE INVENTION

The present invention provides an improved process of synthesizing the multidrug-resistant inhibitor, hydrochloride salt of N-{4-[2-(1,2,3,4-tetrahydro-6,7-dimethoxy-2-isoquinolinyl)-ethyl]phenyl}-9,10-dihydro-5-methoxy-9-oxo-4-acridine carboxamide. This process eliminates the use of prior art coupling reagents which produced a water insoluble diisopropyl urea by-product during the coupling of the intermediates. This urea by-product was not easily removed. The prior art also suggested using a chlorinated solvent, i.e., dichloromethane, during the intermediate synthesis stages.

The present invention further provides an improved process wherein the by-product, tetramethyl urea, formed from the coupled intermediates is water soluble and easily removed. Furthermore, the present inventive process eliminates the use of chlorinated solvents and allows for direct crystallization of the intermediates from the reaction mixture.

The present invention further provides an improved process having increased throughput and products having higher purity.

The present invention includes synthetic steps and intermediates involved in a scheme of synthesizing the hydrochloride salt, N-{4-[2-(1,2,3,4-tetrahydro-6,7-dimethoxy-2-isoquinolinyl)-ethyl]phenyl}-9,10-dihydro-5-methoxy-9-oxo-4-acridine carboxamide of the following formula (I)

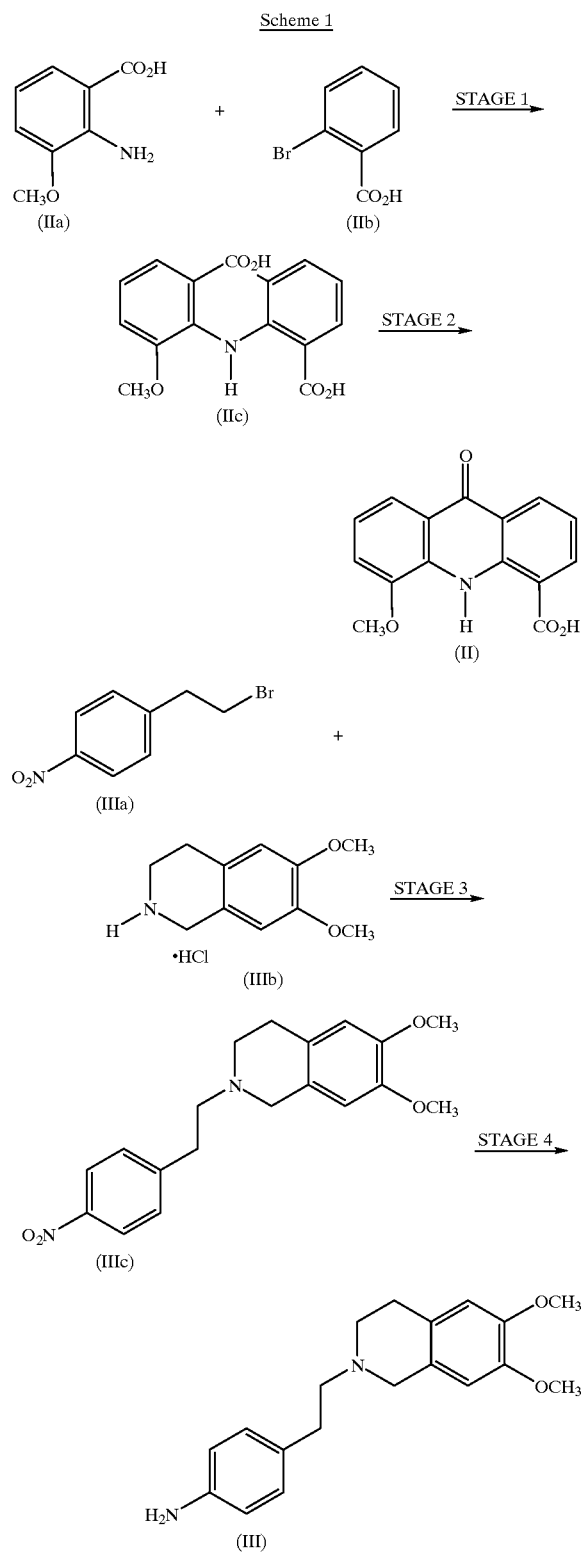

Scheme 2

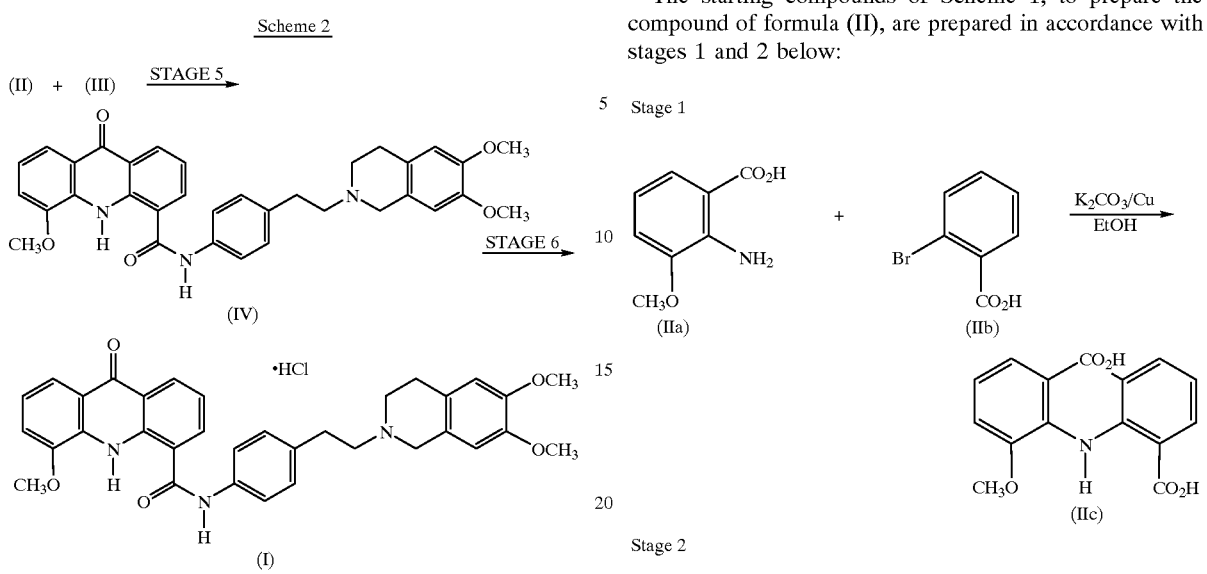

DETAILED DESCRIPTION OF THE INVENTION

In the description and examples that follow throughout the specification, the following abbreviations may be used: THF (tetrahydrofuran); DMF (N,N-dimethyl formamide); TBTU (2-(1H-benzotriazole-1-yl)-1,1,3,3-tetramethyluronium tetrafluoroborate); DMSO (dimethylsulfoxide); g (grams); mL (milliliters); mp (melting point); $^1$H-NMR (proton nuclear magnetic resonance); ppm (parts per million); MHz (Megahertz); and eq. (molar equivalents). Unless otherwise noted, all temperatures are expressed in ° C. (degrees centigrade).

$^1$H-NMR spectra were measured in DMSO using a Bruker ARX-300 MHz instrument. Chemical shifts are expressed in ppm in reference to an internal standard such as DMSO. Apparent multiplicities are designated s, singlet; d, doublet; t, triplet; m, multiplet; br s, broad singlet. Melting points were determined on a Perkin Elmer DSC 7. HPLC data was collected on a Hitachi L-6200 A pump, L-4000 UV detector and a D-2500 integrator.

The materials used in the synthesis process are available from Aldrich Chemical Company, which is located in Milwaukee, Wisconsin. The peptide coupling reagent, TBTU, is available from Peboc, Llangefui, Anglesey, Gwynedd, which is located in Wales, UK. The filtering aid, Harborlite, is available from Harborlite, which is located in Hull, UK.

The synthesis process is carried out in the presence of coupling reagents used in peptide synthesis, such as tetramethyluronium salt based peptide coupling agents and tetramethyluronium salt based acid activating agents. Exemplary agents include, TBTU, O-(Benzotriazole-1-yl)-N,N,N',N'-tetramethyluronium tetrafluoroborate, O-(7-Azabenzotriazole-1-yl)-1,1,3,3-tetramethyluronium hexafluorophosphate and O-(1,2-Dihydro-2-oxo-1-pyridyl)-N,N,N',N'-tetramethyluronium tetrafluoroborate. Other acid activating reagents, such as 1,1'-carbonyidiimidazole, can be utilized in the synthesis process. The synthesis process can be carried out in a alkylamine base, such as triethylamine and diisopropylamine in addition to aromatic amine bases such as pyridine. Suitable solvents for the synthesis process include polar aprotic solvents, such as DMF or 1-methyl-2-pyrrolidinone as well as acetonitrile.

The starting compounds of Scheme 1, to prepare the compound of formula (II), are prepared in accordance with stages 1 and 2 below:

Stage 1

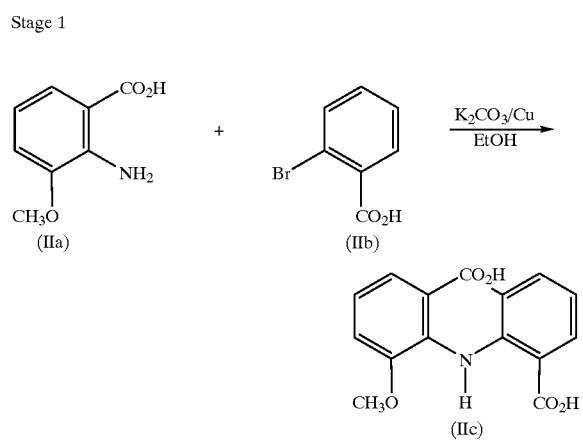

Stage 2

In stage 1, the methoxydiacid of formula (IIc) is obtained by forming a suspension of an 2-amino-3-methoxybenzoic acid (IIa), 2-bromobenzoic acid (IIb) potassium carbonate and copper powder which is stirred in ethanol and heated to reflux for at least 0.5 hours, preferably 1 hour. The suspension is cooled to 20–25° C. and water added. A filtering aid is added and the mixture filtered. The filter bed is washed with water and the combined filtrates adjusted to pH 2–3 by the addition of concentrated hydrochloric acid over a period of about 30 minutes. The resulting suspension is then aged in the reactor at 10–12° C. for at least 1 hour and the solid product collected by filtration, washed with water and dried in a vacuum at 50° C.

In stage 2, the methoxydiacid of formula (IIc), formed in stage 1 is mixed with acetonitrile and heated at reflux and phosphorous oxychloride is added dropwise over 2 hours. The resulting mixture is heated at reflux for at least 1 hour preferably 2 hours. This mixture is then cooled to 10–15° C. Water is added and the resultant thick slurry is heated at reflux for 2.5 hours. The slurry is then cooled to 10° C. and filtered. The product, acridone acid of formula (II), is washed with water followed by acetonitrile and dried in vacuum at 50° C. for 48 hours.

The starting compounds of Scheme 1, to prepare the compound of formula (III), are prepared in accordance with stages 3 and 4 below Stage 3

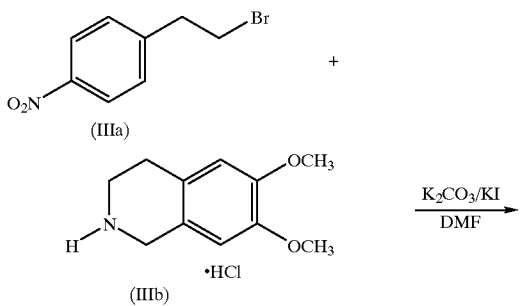

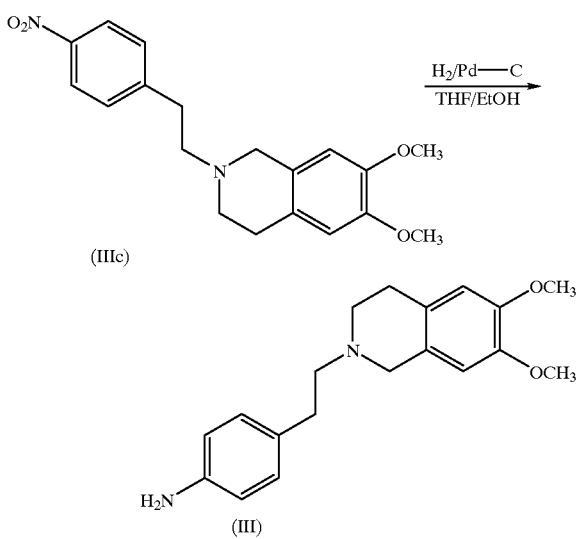

Stage 5

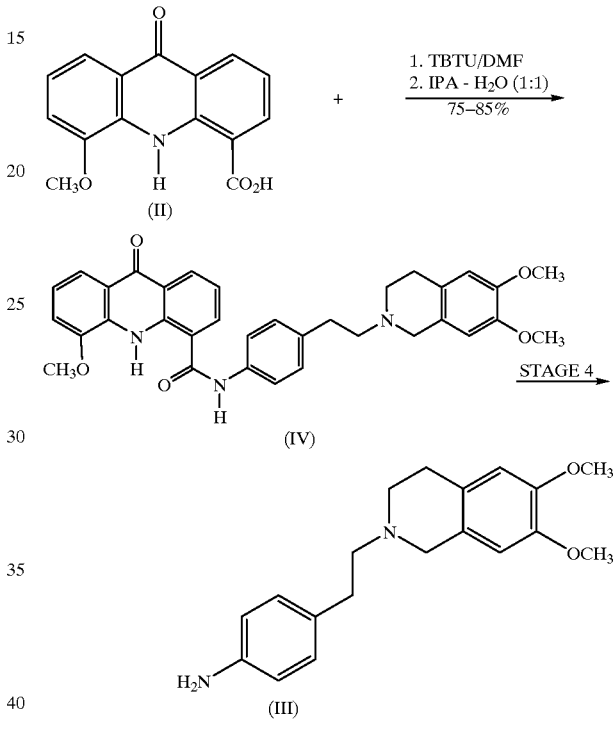

In stage 3, the nitrophenethyl isoquinoline of formula (IIIc) is obtained by mixing 4-nitrophenethyl bromide, of formula (IIIa), 6,7-dimethoxy-1,2,3,4-tetrahydroisoquinoline hydrochloride, of formula (IIIb), anhydrous potassium carbonate and potassium iodide in DMF. The mixture is heated at 70° C. with stirring under a nitrogen atmosphere for 18 hours. The mixture is cooled to 50° C. and methanol added. The mixture is further cooled to 30° C. and water added. The mixture is then stirred at 10° C. for 1 hour, filtered, and the product washed with water and dried at 45° C. under vacuum In stage 4, the nitrophenethyl isoquinoline, or formula (IIIc), formed in stage 3 is stirred in a solution of ethanol and THF at 15–20° and purged with nitrogen and a Pd/C catalyst added. After re-purging with nitrogen, the stirring is stopped and the mixture is purged with hydrogen. Stirring is resumed and the mixture maintained at 15–25° C. until hydrogen uptake is complete. The reaction mixture is filtered, the filters rinsed with THF and the combined filtrates concentrated to an appropriate volume under vacuum at 55–65° C. Hexane is added over a 2040 minute period and the resulting slurry cooled to 0° C. After stirring at 0° C. for 1.5 hours, the suspension is filtered, the solid washed with hexane and dried in a vacuum oven at 40–45° C. The resulting solid is aminophenethyl isoquinoline of formula (III).

The intermediate compounds of scheme 1, to prepare the multidrug inhibitor free base compound of formula (IV) is prepared in accordance with stage 5.

In stage 5, Scheme 2, a mixture of the intermediate compounds, acridone acid of formula (II) and aminophenethyl isoquinoline of formula (III) are stirred in DMF under a nitrogen atmosphere until complete dissolution is accomplished in about 10 minutes. A peptide coupling reagent, TBTU, is added followed by triethylamine, a base. The solution is stirred at 20–25° C. for 1–2 hours until the reaction is complete. A mixture of isopropanol-water is added and the mixture stirred at 20–25° C. for 30–60 minutes until crystallization occurs. The resulting slurry, MDRI free base of formula (IV), is filtered and washed with methanol, followed by water and dried in a vacuum oven at up to 50° C.

The crude MDRI free base is then recrystallized by dissolving in DMF at 35–40° C. followed by the addition of ethanol over a period of about 4 hours at 35–40° C. The resulting slurry is then cooled at 10° C. for 1 hour and filtered. The product is washed with methanol and dried in a vacuum oven at up to 50° C.

The compound of formula (I) in scheme 2, wherein the MDRI free base of formula (Iv) is converted into a hydrochloride salt of formula (I) in accordance with stage 6.

Stage 6

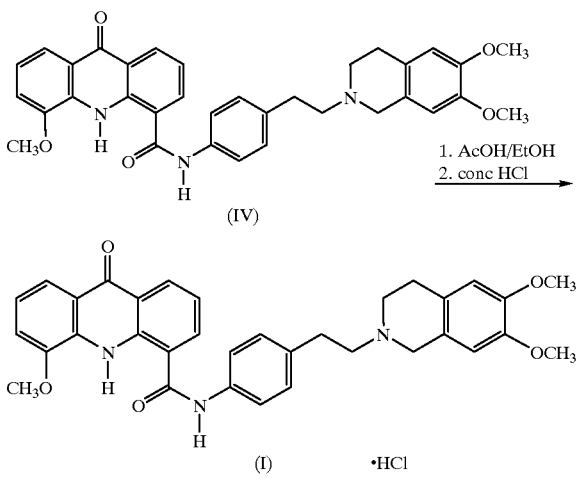

In stage 6, a stirred suspension of the MDRI free base of formula (Iv) in glacial acetic acid is heated to 65–70° C. and the resulting solution hot filtered. The solution is then reheated to 70° C. and hot, pre-filtered ethanol is added. Pre-filtered concentrated hydrochloric acid is then added over a period of about 30 minutes. The resulting solution is stirred at 70° C. until crystals form, about 20 minutes, and then cooled to 20–25° C. over 1 hour and filtered. The resulting filter cake is washed with ethanol and dried for at least 70 hours at 65° C. in a vacuum oven.

EXAMPLES

Example 1

Methoxydiacid (Formula IIc)

A suspension of 164.6 g (1 molar eq) of 2-amino-3-methoxybenzoic acid (formula IIa), 217.7 g (1.1 molar eq) of 2-bromobenzoic-acid (formula IIb), 272.3 g (2.0 molar eq) of potassium carbonate and 12.5 g (0.2 molar eq) of copper powder is stirred in 1500 mL of ethanol and heated to reflux for 0.5–3 hrs, preferably 1 hour. The suspension is cooled to 20–25° C. and 1450 mL of water is added. A filtering aid, 15 g, is added and the mixture filtered. The filter bed is washed with 875mL of water and the combined filtrates adjusted to a pH of 2–3 by the addition of 250 mL of concentrated hydrochloric acid over a period of about 30 min. The resulting suspension is then aged in the reactor at 10–12° C. for at least 1 hour and the solid product collected by filtration, washed with 1450 mL of water and dried in a vacuum at 50° C. The expected yield of the titled compound is 95% theoretical.

$^1$H-NMR (300 MHz): δ 3.7 (s, 3H, OMe); 6.1–7.9 (m, 7H, Ar); 9.7 (br s, 1H, COOH); 11.1 (br s, 1H, COOH) ppm. Mp is 254–256° C.

Example 2

Acridone Acid (Formula II)

A mixture of 280.0 g (1 molar eq) of methoxydiacid (formula IIc) in 2300 mL of acetonitrile is heated at reflux and 200 mL (2.2 molar eq) of phosphorous oxychloride added dropwise over 2 hours. The mixture is heated at reflux for 1–5 hours, preferably 2 hours. The mixture is then cooled to 10–15° C. To the mixture 1700 mL of water is added and the resultant thick slurry is heated at reflux for 2.5 hours. The slurry is then cooled to 10° C. and filtered. The resulting product is washed twice with 850 mL of water, washed twice with 850 mL of acetonitrile and dried in vacuum at 50° C. for 48 hours. The expected yield of the titled compound is 95% theoretical.

$^1$H-NMR (300 MHz): δ 4.0 (s, 3H, OMe); 6.9–8.5(m, 7H, 6Ar and NH); 10.1 (br s, 1H, COOH) ppm. Mp is 354–362° C.

Example 3

Nitrophenethyl Isoquinoline (Formula IIIc)

A mixture of 302 g (1 molar eq) of 4-nitrophenethyl bromide (formula IIIa), 302 g (1 molar eq) of 6,7-dimethoxy-1,2,3,4-tetrahydroisoquinoline hydrochloride (formula IIIb), 181 g (1.1 molar eq) of anhydrous potassium carbonate and 45 g (0.2 molar eq) of potassium iodide in 1500 mL of DMF is heated at 70° C. with stirring under a nitrogen atmosphere for 12–24 hours, preferably 18 hours. The mixture is cooled to 50° C. and 450 mL of methanol is added. The mixture is then cooled to 30° C. before adding 3000 mL of water. The mixture is stirred at 10° C. for 1 hour, filtered and the product washed twice with 1500 mL of water and dried at 45° C. under vacuum. The expected yield of the titled compound is 90% theoretical.

$^1$H-NMR (300 MHz): δ 2.53–3.0 (m, 8H, CH$_2$); 3.5 (s, 2H, N—CH$_2$—Ph); 3.7 (s, 6H, Ome); 6.4 (d, 2H, Ar isoquinoline); 7.2 and 7.9 (dd, 4H, Ar PHNO$_2$) ppm. Mp is 116–118° C.

Example 4

Aminophenethyl Isoquinoline (Formula III)

A stirred solution of 230.0 g (I molar eq) of nitrophenethyl isoquinoline (formula IIIc) in 1700 mL of ethanol and 1700 mL of THF at 15–20° C. is purged with nitrogen and 46 g of Pd/C catalyst is added. After re-purging with nitrogen, the stirring is stopped and the mixture is purged with hydrogen. Stirring is resumed and the mixture is maintained at 15–25° C. until hydrogen uptake is complete (1–20 hours). The reaction mixture is filtered, the filter is rinsed with 900 mL of THF and the combined filtrates are then concentrated to 7 volumes under vacuum at 55–65° C. To the concentrated filtrate is added 2000 mL of hexane over 20–40 minutes, and the resulting slurry cooled to 0° C. After stirring at 0° C. for 1.5 hours the suspension is filtered, the solid washed with 450 mL of hexane and dried in a vacuum oven at 40–45° C. The expected yield of the titled compound is 89% theoretical.

$^1$H-NMR (300 MHz) δ 2.5–3.0 (m, 8H, CH$_2$); 3.5 (s, 2H, N—CH$_2$—Ph); 3.7 (s, 6H, OMe); 6.4 (d, 2H, Ar isoquinoline); 7.2 and 7.9 (dd, 4H, Ar PHNO$_2$) ppm. Mp is 123–126° C.

Example 5

MDRI Free Base-(Formula IV)

A mixture of 200.0 g (1 molar eq) of acridone acid (formula II) and 232.1 g (1 molar eq) of aminophenethyl isoquinoline (formula III) stirred in 2000 mL of DMF at 20–25° C. until complete dissolution is accomplished in about 10 minutes. To this mixture 250.5 g (1.05 molar eq) of TBTU, a peptide coupling reagent, is added, followed by 218 mL (2.1 molar eq) of triethylamine, a base. The resulting solution is stirred at 20–25° C. for 1–2 hours until the reaction is complete. A 1:1 mixture of 12000 mL of isopropanol and 1000 mL of water is added and the mixture stirred at 20–25° C. until crystallization occurs (30–60 minutes). The resulting slurry is filtered and washed with 1600 mL of methanol, followed by washing with 1600 mL of water. The slurry is dried in a vacuum oven at up to 50° C.

The crude MDRI free base (formula IV) is then recrystallized by dissolving in 1800 mL of DMF at 35–40° C., followed by the addition of 3600 mL of ethanol over a period of about 4 hours at 35–40° C. The resulting slurry is then cooled to 10° C. for 1 hour and filtered. The product is washed with 1000 mL of methanol and dried in a vacuum oven at up to 50° C. The expected yield of the titled compound is 70–75% theoretical.

$^1$H-NMR (300 MHz): δ 2.40–2.95 (m, 8H, CH$_2$); 3.58 (s, 2H, N—CH$_2$—Ph); 3.72 (s, 6H, 2OMe); 4.05 (s, 3H, OMe acridone); 6.78 (d, 2H, Ar isoquinoline); 7.20–7.88 (m, 8H, Ar); 8.48 (t, 2K, H$_2$ and H$_7$ acridone); 10.60 (br s, 1H, CONK); 12.32 (br s, 1H, NH acridone) ppm. Mp is 215–220° C.

Example 6

MDRI Drug Substance (Formula I)

A stirred suspension of 20.0 g (1 molar eq) of MDRI free base (formula IV) in 80 mL of glacial acetic acid is heated to 65–70° C. and the resulting solution hot filtered. The solution is then reheated to 70° C. and 240 mL of pre-filtered ethanol (70° C.) is added. To this solution, 4.4 mL (1.5 molar eq) of pre-filtered concentrated hydrochloric acid is added over a period of about 30 minutes. The resulting solution is stirred at 70° C. until crystals form, about 20 minutes, and cooled to 20–25° C. over a 1 hour period and filtered. The resulting filter cake is twice washed with 120 mL of ethanol and dried for at least 70 hours at 65° C. in a vacuum oven. The expected yield of the titled compound is 90% theoretical.

$^1$H-NMR (500 MHz, DMSO-d$_6$) δ 12.31 (s, 1H), 10.98 (brs, 1H), 10.75 (s, 1H), 8.53 (dd, 1H), 8.52 (ddd, 1H), 7.82 (ddd, 1H), 7.76 (m, 2H), 7.44 (dd, 1H), 7.40 (dd, 1H), 7.38 (m, 2H), 7.28 (dd, 1H), 6.84 (s, 1H), 6.81 (s, 1H), 4.52 (d, 1H), 4.29 (dd, 1H), 4.06 (s, 3H) 3.77 (m, 1H), 3.76 (s, 3H), 3.75 (s, 3H), 3.45 (m, 2H), 3.33 (m, 1H), 3.19 (m, 1H), 3.19 (m, 2H), 2.96 (dt, 1H) ppm. Mp is 240° C.

Anal. Calc'd. for C$_{34}$H$_{33}$N$_3$O$_5$.HCl.0.5H$_2$O: C, 67.04; H, 5.57; N, 6.90; Cl, 5.82;

Found: C, 67.00; H, 5.78; N, 6.89; Cl, 5.87.

What is claimed is:

1. A method of synthesizing a compound of formula (IV)

(IV)

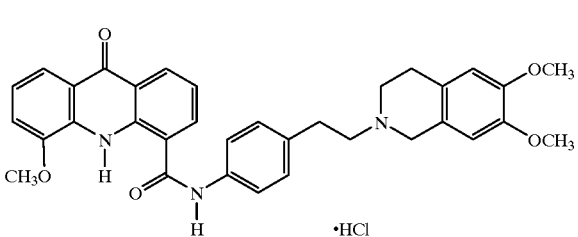

which comprises the steps of:

(i) dissolving a compound of formula (II):

(II)

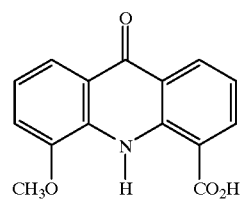

and a compound of formula (III):

(III)

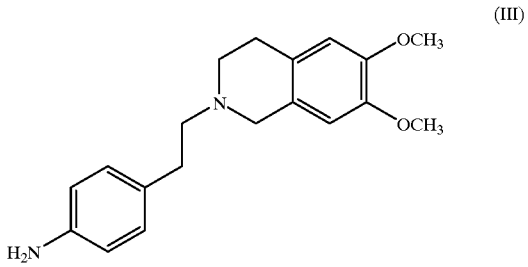

in a polar aprotic solvent;

(ii) reacting said compounds of formula (II) and (III) dissolved in said solvent in the presence of a tetramethyluronium based peptide coupling reagent and an alkylamine to form a product mixture; and (iii) crystallizing directly from the product mixture a product comprising a free base of formula IV;

(iv) optionally converting the compound of formula (IV) to the HCl salt of formula (I)

(I)

2. The method of claim 1, wherein the coupling reagent is 2-(1H-benzotriazole-1-yl)-1,1,3, 3-tetramethyluronium tetrafluoroborate.

3. The method of claim 1, wherein the alkylamine base is triethylamine.

4. The method of claim 1, wherein the reaction takes place at about 20–25° C.

5. The method of claim 1, wherein the reaction takes place in a period of at least one hour.

6. The method of claim 1, wherein said coupling step is conducted at about 20–25° C.

7. The method of claim 1, wherein the polar aprotic solvent is dimethyl formamide.

8. The method of claim 1, wherein the compound of formula IV is converted to the HCl salt of formula I.

* * * * *